US012778650B2

(12) United States Patent
Gosik-Wolfe

(10) Patent No.: US 12,778,650 B2
(45) Date of Patent: Nov. 3, 2026

(54) SURGICAL TOOL AND HANDLE FOR A SURGICAL TOOL

(71) Applicant: Shukla Medical, St. Petersburg, FL (US)

(72) Inventor: Adam Gosik-Wolfe, Tampa, FL (US)

(73) Assignee: Shukla Medical

( * ) Notice: Subject to any disclaimer, the term of this patent is extended or adjusted under 35 U.S.C. 154(b) by 322 days.

(21) Appl. No.: 18/184,150

(22) Filed: Mar. 15, 2023

(65) Prior Publication Data

US 2023/0293213 A1 Sep. 21, 2023

Related U.S. Application Data

(60) Provisional application No. 63/320,020, filed on Mar. 15, 2022.

(51) Int. Cl.
*A61B 17/88* (2006.01)
*A61B 17/00* (2006.01)

(52) U.S. Cl.
CPC .. *A61B 17/8847* (2013.01); *A61B 2017/0046* (2013.01)

(58) Field of Classification Search
CPC ..... A61B 17/16; A61B 17/1604; A61B 17/88; A61B 17/8802; A61B 17/8847; A61B 2017/0046; B25G 3/12; B25G 3/18; B25G 3/20; B25G 3/24
See application file for complete search history.

(56) References Cited

U.S. PATENT DOCUMENTS

| | | | | | |
|---|---|---|---|---|---|
| 5,735,855 | A * | 4/1998 | Bradley | A61B 17/1604 | 606/86 R |
| 5,827,290 | A * | 10/1998 | Bradley | A61B 17/1604 | 606/85 |
| 6,010,508 | A * | 1/2000 | Bradley | A61B 17/92 | 606/86 R |
| 6,139,214 | A * | 10/2000 | Zirps | A61B 17/162 | 403/328 |
| D458,995 | S * | 6/2002 | Lang | D24/147 | |
| 7,467,575 | B2 * | 12/2008 | Lai | B25G 3/18 | 81/177.85 |
| 7,587,791 | B2 * | 9/2009 | Liou | B25D 3/00 | 81/177.1 |
| 9,255,591 | B2 * | 2/2016 | Carnevali | F16B 1/00 | |

(Continued)

FOREIGN PATENT DOCUMENTS

| | | | | |
|---|---|---|---|---|
| DE | 69737509 T2 * | 12/2007 | A61B 17/151 |
| EP | 3613367 A1 * | 2/2020 | A61B 17/00 |

(Continued)

OTHER PUBLICATIONS

Extended European Search Report and Written Opinion in counterpart European Application No. 23161912.3, mailed Jul. 13, 2023.

*Primary Examiner* — Eric S Gibson
(74) *Attorney, Agent, or Firm* — Kim IP Law Group LLC

(57) ABSTRACT

A surgical tool including a handle having a grip with a proximal end, a distal end and a through-bore, a coupler coupled to the distal end of the grip, a plunger slidably positioned within the through-bore of the grip, and a biasing member in the through-bore of the grip to bias the plunger distally into the coupler; and a bit releasably coupled to the coupler of the handle.

21 Claims, 17 Drawing Sheets

(56) References Cited

U.S. PATENT DOCUMENTS

| | | | | | |
|---|---|---|---|---|---|
| 9,772,001 | B2 * | 9/2017 | Yang | F16F 13/005 | |
| 10,092,302 | B2 * | 10/2018 | Overes | B25G 3/18 | |
| 10,098,445 | B1 * | 10/2018 | Morad | B25G 3/24 | |
| 10,524,804 | B2 * | 1/2020 | Clark | A61B 17/1604 | |
| 10,843,325 | B2 * | 11/2020 | Scheuber | B25G 3/04 | |
| 11,154,306 | B2 * | 10/2021 | Sweitzer | A61B 17/1675 | |
| 11,440,177 | B2 * | 9/2022 | Sweitzer | A61B 17/92 | |
| 11,772,255 | B2 * | 10/2023 | Scheuber | B25G 3/18 | 403/321 |
| 12,023,052 | B2 * | 7/2024 | Tyndall | A61B 17/1626 | |
| 12,035,923 | B2 * | 7/2024 | Sweitzer | B23B 31/20 | |
| 2014/0288566 | A1 * | 9/2014 | Green, II | A61B 17/92 | 606/99 |
| 2016/0157871 | A1 * | 6/2016 | Overes | A61B 17/16 | 279/82 |
| 2018/0257214 | A1 * | 9/2018 | Scheuber | B25G 3/18 | |
| 2019/0201008 | A1 * | 7/2019 | Sweitzer | A61B 17/92 | |
| 2020/0015829 | A1 * | 1/2020 | Khalili | A61B 17/320758 | |
| 2020/0060693 | A1 * | 2/2020 | Sweitzer | A61B 17/1613 | |
| 2021/0038205 | A1 * | 2/2021 | Milella Jr. | B25G 3/20 | |
| 2021/0038206 | A1 * | 2/2021 | Milella, Jr. | B25G 3/18 | |
| 2021/0039244 | A1 * | 2/2021 | Milella, Jr. | B25G 1/102 | |
| 2021/0068851 | A1 * | 3/2021 | Sweitzer | A61B 17/1735 | |
| 2021/0298917 | A1 * | 9/2021 | Sweitzer | B25G 1/102 | |
| 2022/0039807 | A1 * | 2/2022 | Sweitzer | B23B 31/20 | |
| 2022/0211392 | A1 * | 7/2022 | Bibard | A61B 17/92 | |
| 2023/0240734 | A1 * | 8/2023 | Stroh | A61B 17/8847 | 606/80 |
| 2023/0293213 | A1 * | 9/2023 | Gosik-Wolfe | A61B 17/1604 | 606/53 |
| 2024/0277348 | A1 * | 8/2024 | Sweitzer | A61B 17/00 | |
| 2024/0277349 | A1 * | 8/2024 | Sweitzer | B23B 31/20 | |

FOREIGN PATENT DOCUMENTS

| | | | | | |
|---|---|---|---|---|---|
| EP | 3771441 | A1 * | 2/2021 | A61B 17/1659 |
| EP | 3888579 | A1 * | 10/2021 | A61B 17/92 |
| EP | 3613367 | B1 * | 8/2023 | A61B 17/00 |
| EP | 4218621 | A1 * | 8/2023 | A61B 17/1604 |
| EP | 4245230 | A1 * | 9/2023 | A61B 17/1604 |
| EP | 3888579 | B1 * | 12/2024 | A61B 17/92 |
| WO | WO-9817210 | A1 * | 4/1998 | A61B 17/151 |
| WO | WO-2015006876 | A1 * | 1/2015 | A61B 17/16 |
| WO | WO-2018165083 | A2 * | 9/2018 | A61B 17/162 |
| WO | WO-2021018908 | A1 * | 2/2021 | A61B 17/1659 |

* cited by examiner

SURGICAL TOOL AND HANDLE FOR A SURGICAL TOOL

CROSS-REFERENCE TO RELATED APPLICATIONS

This application claims the benefit under 35 U.S.C. § 119(e) to U.S. Provisional Application No. 63/320,020, filed Mar. 15, 2022, the entire disclosure of which is hereby incorporated by reference for all purposes.

BACKGROUND OF THE DISCLOSURE

Surgical implants implanted into patients during orthopedic surgeries sometimes require removal, for example, when an implant breaks or an infection sets in. Removal of an implant may require removal of cement used to affix the implant to bone. Surgeons have access to a wide variety of tools for removing cement, including surgical osteotomes, gouges, hooks, taps, drills, rongeurs and chisels. There is a need for an ergonomic and light-weight surgical tool and handle for a surgical tool for use in orthopedic surgeries and, particularly, for use in chipping away cement from implants to be removed from a patient.

SUMMARY OF THE DISCLOSURE

In accordance with an exemplary embodiment of the subject disclosure, a handle for a surgical tool is provided. The handle includes a grip with a proximal end, a distal end and a through-bore, a coupler coupled to the distal end of the grip, a plunger slidably positioned within the through-bore of the grip, and a biasing member in the through-bore of the grip to bias the plunger. According to an aspect, the handle further comprises a quick connect about its distal end.

In accordance with another exemplary embodiment of the subject disclosure, a surgical tool is provided. The surgical tool comprises the aforementioned handle and a bit releasably coupled to the coupler of the handle.

According to an aspect, the bit is a chisel bit. According to another aspect, the coupler comprises a longitudinal bore and the bit includes a key releasably lockable in the longitudinal bore. According to another aspect, the longitudinal bore has a cross-section sized to substantially match that of the key. According to another aspect, the longitudinal bore and the key are substantially oval-shaped in cross-section. According to another aspect, the key includes a proximal end, a distal end, and a mid-portion circumscribed by a locking channel. According to another aspect, the coupler further comprises a button slidably positioned in the coupler. According to another aspect, the button includes a bore alignable with the longitudinal bore of the coupler and a locking tab releasably engageable with the locking channel. According to another aspect, the surgical tool further comprises a second biasing member for biasing the locking tab into engagement with the locking channel. According to another aspect, wherein, when the bit is inserted and locked within the coupler, the first biasing member biases the plunger to exert force against the bit.

According to an aspect, the surgical tool further comprises a cap coupled to the distal end of the grip. According to another aspect, the cap includes a strike plate. According to another aspect, the cap includes threads for threadedly engaging threads provided on the grip.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION

Figure 1:
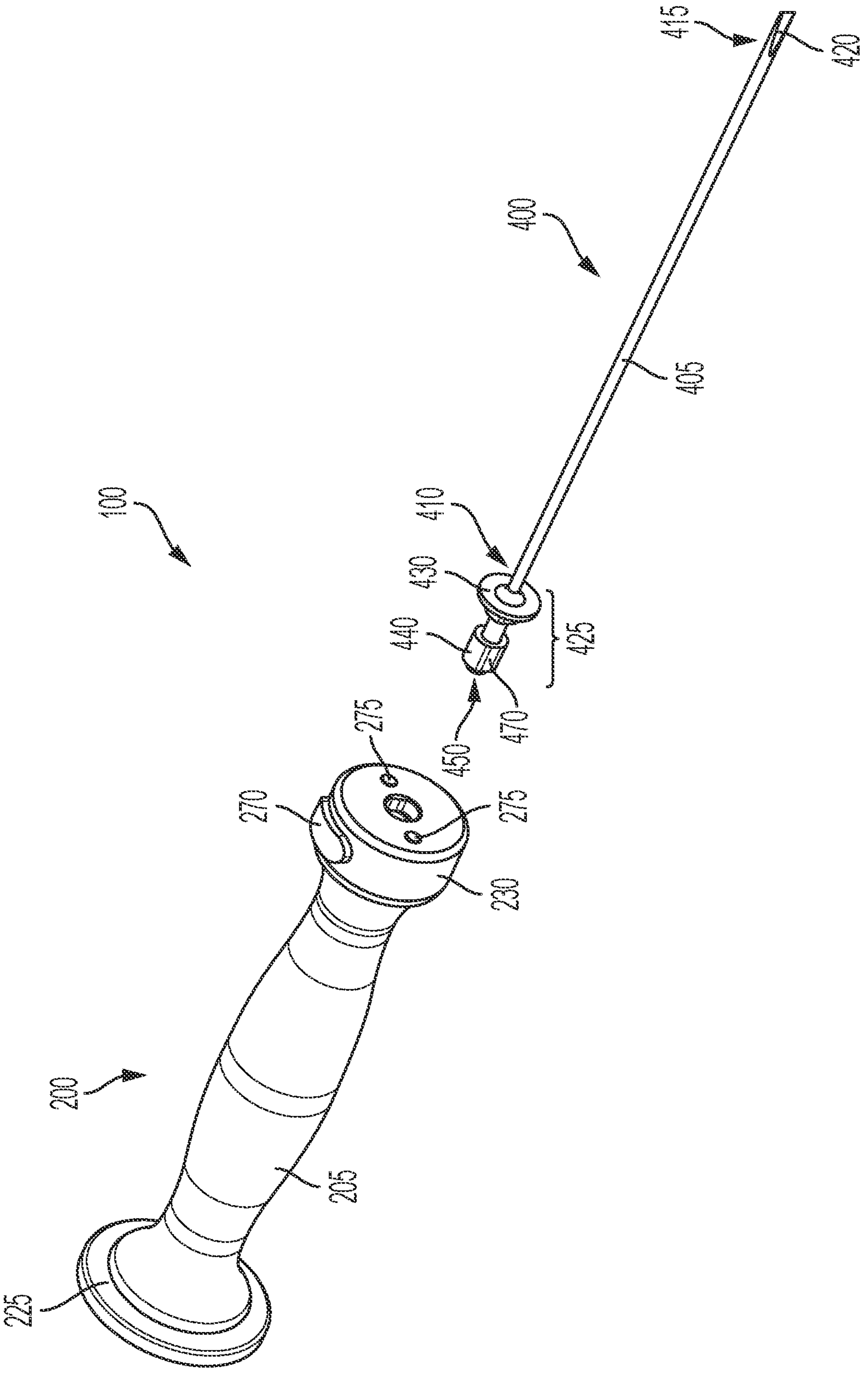
FIG. 1 is an exploded perspective view of a surgical tool in accordance with an exemplary embodiment of the subject disclosure.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

"Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more exemplary embodiments. One skilled in the relevant art will recognize, in light of the description herein, that the subject disclosure can be practiced without one or more of the specific features or advantages of a particular exemplary embodiment. In other instances, additional features and advantages may be recognized in certain exemplary embodiments that may not be present in all exemplary embodiments of the present disclosure.

Referring now to the Figures, there is shown a surgical tool 100 in accordance with an exemplary embodiment of the subject disclosure. Surgical tool 100 may be used during an orthopedic surgery, for example, to chip away bone cement used in a shoulder, elbow or other implant. Surgical tool 100 includes a handle 200 and a bit 400 releasably coupled to handle 200. In the embodiments depicted in the Figures, bit 400 is a chisel bit 400 for use in orthopedic surgery, though it should be appreciated that handle 200 may couple to other types of bits, e.g., osteotomes, and that various embodiments described and claimed herein are not intended to be limited to any particular type of bit or use of surgical tool 100.

As best shown in FIGS. 1-5, bit 400 includes an elongated shaft 405 having a proximal end 410 and a distal end 415 provided with a tapered blade 420, and a connector 425 at proximal end 410 of shaft 405 for coupling to handle 200. Connector 425 includes a disk 430 having a proximally facing annular face 435 arranged perpendicularly with respect to shaft 405 and a key 440 having an overall oval-shape. Disk 430 has a diameter $D_1$ of about 12.4 mm (see FIG. 5), though it should be appreciated disk 430 may have a smaller or larger diameter, including, e.g., a diameter $D_1$ of about 8 to 27 mm, such as, e.g., 8, 9, 10, 11, 12, 13, 14, 15, 16, 17, 18, 19, 20, 21, 22, 23, 24, 25, 26, or 27 mm. Key 440 includes a distal end 445 adjacent to disk 430, a proximal end 450 provided with a tapered cone 455, a reduced diameter mid-portion defining a locking channel 465 and flat guide surfaces 470 on opposed sides of distal and proximal ends 445, 450 of key 440. As shown in the Figures, the various constituent parts of bit 400 are formed integrally into a single piece, though it should be appreciated that bit 400 may be assembled from individual constituent parts. It should also be appreciated that bit 400 may be constructed from any materials suitable for its intended purpose, such as, for example, metals and metal alloys capable of withstanding high-force impacts typical in operation of surgical chisels.

As best shown in FIGS. 1, 2, 6 and 8, handle 200 includes an elongated grip 205 having a proximal end 210, a distal end 215 and a longitudinal through-bore 220 with internal threads 222 at proximal end 210, a cap 225 coupled to proximal end 210 of grip 205, a coupler 230 coupled to distal end 215 of grip 205, a plunger 235 slidably positioned with through-bore 220 at distal end 215 of grip 205, and a first biasing member 240 (e.g., a compression spring 240 an elastomer and the like) within through-bore 220 for biasing plunger 235 distally into coupler 230. In the embodiments illustrated in the Figures, grip 205 is hour-glass shaped to improve grasping by a user, such as a surgeon, though it should be appreciated that grip 205 may be shaped differently and/or be provided with other features for improving a user's grasp, such as, for example, stippling, texturing, a rubber coating, or the like. In accordance with one aspect of the subject disclosure, handle 200 has an overall length $L_1$ of about 127 mm (see FIG. 2) but can be less than or greater than 127 mm, e.g., 110, 112, 114, 116, 118, 120, 122, 124, 126, 127, 128, 129, 130, 131, 132, 133, 134, 135, 136, 137, 138, 139, 140, 141, 142, 143, 144, 145, 146, 147, 148, 149, or 150 mm.

Cap 225 includes a disk-shaped strike plate 245, a cylindrical stop 250 extending distally and coaxially from strike plate 245 and having an outer surface provided with threads 255 and a distally facing annular face 260, and a smooth and cylindrical alignment post 262 extending distally from annular face 260 of stop 250. The cap includes threads 255 for threadedly engaging threads 222 provided on the grip 205. That is, threads 255 of stop 250 engage with threads 222 of grip 205 in screw-like fashion to secure cap 225 to proximal end 210 of grip 205, though it should be appreciated that cap 225 may be secured to grip 205 in other ways. For example, with respect to some embodiments, cap 225 is both screwed and welded to grip 205, whereas in other embodiments, cap 225 is only welded to grip 205. It should be appreciated, however, that various embodiments described and claimed herein are not intended to be limited to any particular method or manner of securing cap 225 to grip 205. The cap has a planar distally facing end and an overall width greater than an overall width of the handle.

Coupler 230 includes a quick connect including a button 270, second biasing members 280, a longitudinal bore 305 in the coupler, and a bore 330 in the button for easily connecting with a corresponding male quick connect. The coupler includes a main body 265, the button 270 slidably positioned within main body 265, stop posts 275 for limiting movement of button 270 within main body 265 and the second biasing members 280 for biasing button 270. Coupler 230 further comprises the longitudinal bore 305 and the key 440 of the bit 400 is releasably lockable in the longitudinal bore 305.

As best shown in FIGS. 1, 2 and 10-12, main body 265 includes a tapered and curved proximal end 285, a flat distally facing end 290, an outer surface 292, a cylindrically shaped grip receptacle 295 at proximal end 285 for coupling to distal end 215 of grip 205, and a plunger receptacle 300 positioned distally of and in fluid communication with the grip receptacle 295 for receiving the distal end of plunger 235. The longitudinal bore 305 communicates with and extends distally from plunger receptacle 300 to distal end 290, a blind button receptacle 315 extends from outer surface 292 and intersects longitudinal bore 305 at about a right-angle, and cylindrical and opposed post bores 320 extend proximally from distal end 290 and intersect respective sides of button receptacle 315. Cylindrical grip receptacle 295 slides over and is attached or connected to distal end 215 of grip 205, though it should be appreciated that grip receptacle 295 may couple to grip 205 in other ways. For example, grip receptacle 295 may be sized to tightly receive distal end 215 of grip 205 to enable a press-fit coupling of main body 265 to grip 205. In an alternative embodiment, grip receptacle 295 and distal end 215 of grip 205 are provided with helical threads to permit screw-like coupling. In still other embodiments, pins or screws are provided for coupling main body 265 to grip 205.

Longitudinal bore 305 of main body 265 has a cross-section sized to substantially match that of key 440 of bit 400 to allow bore 305 to closely receive bit 400 when surgical chisel 100 is fully assembled. In the embodiments described herein, for example, longitudinal bore 305 has a substantially oval shape with opposed flat side surfaces 310 for closely receiving guide surfaces 470 of key 440. In this manner, side surfaces 310 ensure that bit 400 (and, in particular, tapered blade 420) is properly aligned rotationally with respect to handle 200 when bit 400 is coupled thereto. Longitudinal alignment of bit 400 is maintained by a close fit between longitudinal bore 305 and key 440, as well as by annular face 435 of disk 430 which closely engages flat distal end 290 of main body 265 to ensure that shaft 405 of bit 400 is maintained in proper longitudinal orientation relative to handle 200. Of course, it will be appreciated that bore 305 and key 440 may be provided with differently shaped cross-sections and alignment features, and that various embodiments described and claimed herein are not intended to be limited to any particular cross-section(s) or other features for receiving, aligning and/or orientating bit 400 relative to handle 200.

Button 270 is slidably positioned within button receptacle 315 of coupler 230 and includes a curved top surface 325, the bore 330, a locking tab 335 adjacent to a side of bore 330 opposite the curved top surface 325 of the button 270, grooves 342 on opposed sides of the button, and downwardly facing lower flat surfaces 340. The bore 330 is alignable with the longitudinal bore 305 of the coupler and the locking tab 335 is releasably engageable with the locking channel 465 of bit 400 when assembled together. Stop posts 275 are positioned within post bores 320 of main body 265 and communicate respectively with grooves 342 of button 270 to limit movement of button 270 within main body 265 between an unlocked position, at which bore 330 of button 270 aligns with longitudinal bore 305 of main body 265 to permit free insertion/removal of bit 400 into/from coupler 230 (see FIG. 15), and a locked position, at which locking tab 335 of button 270 engages locking channel 465 of bit 400 to lock and maintain bit 400 within coupler 230 (see FIG. 16). Second biasing members 280 are positioned at the bottom of button receptacle 315 and respectively engage flat surfaces 340 of button 270 to bias button 270 into the locked position. In the embodiments described herein, biasing members 280 are compression springs, though it should be appreciated that other biasing members may be used, such as, for example, leaf springs, wave springs, elastomers, or the like.

Figure 2:
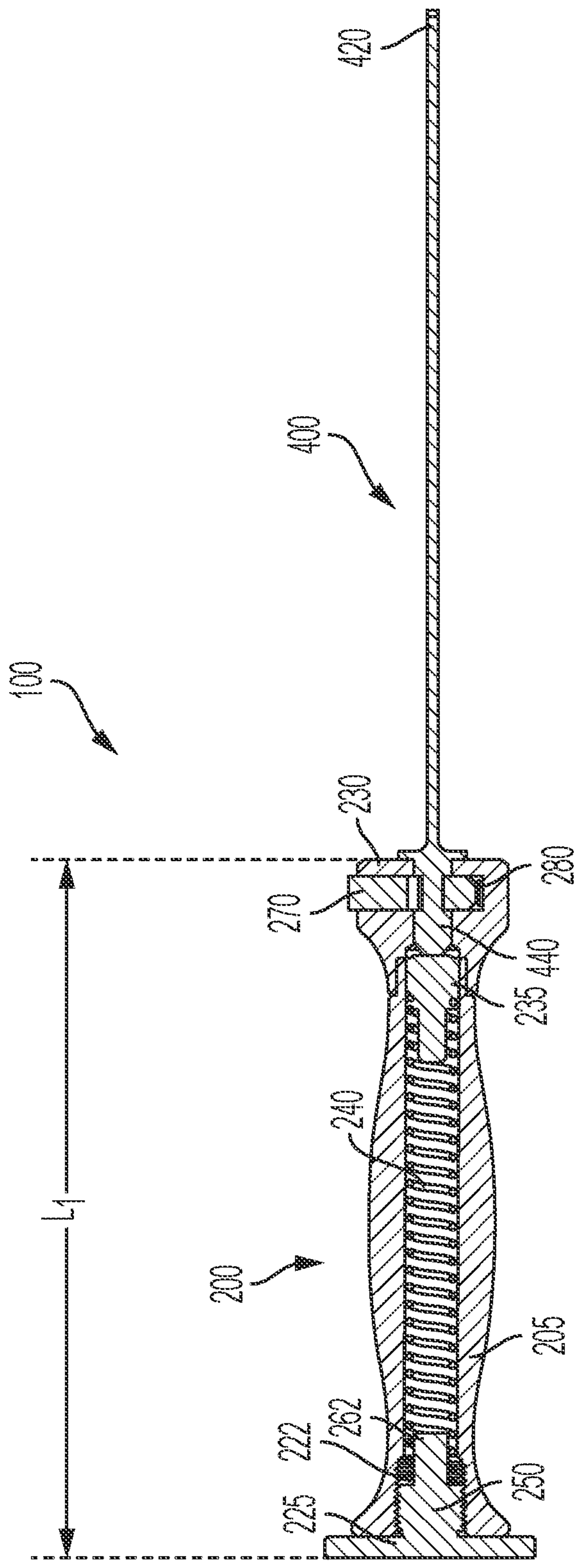
FIG. 2 is a side sectional view of the surgical tool of FIG. 1 in an assembled state.
Figure 3:
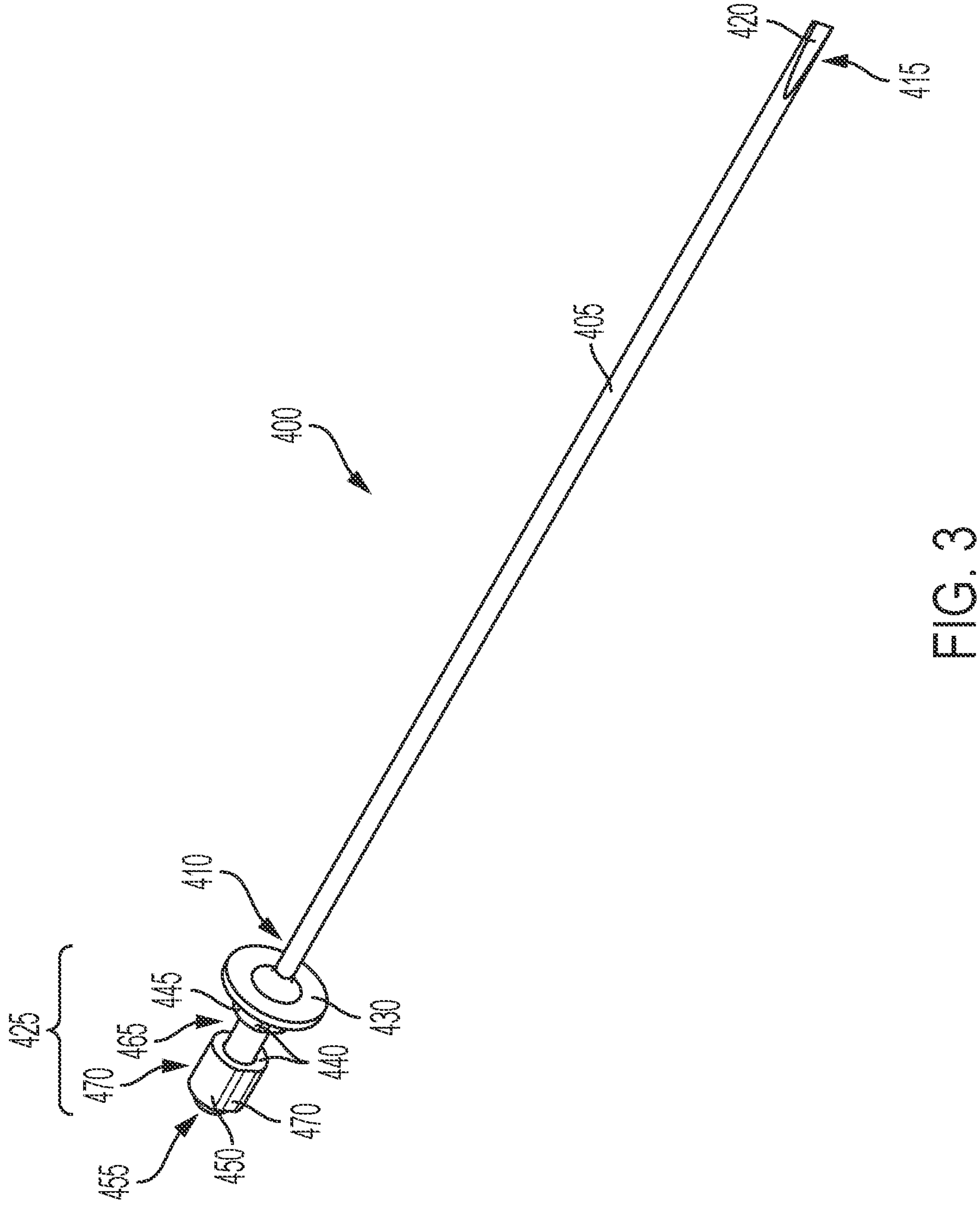
FIG. 3 is a perspective view of a bit of the surgical tool of FIG. 1.
Figure 4:
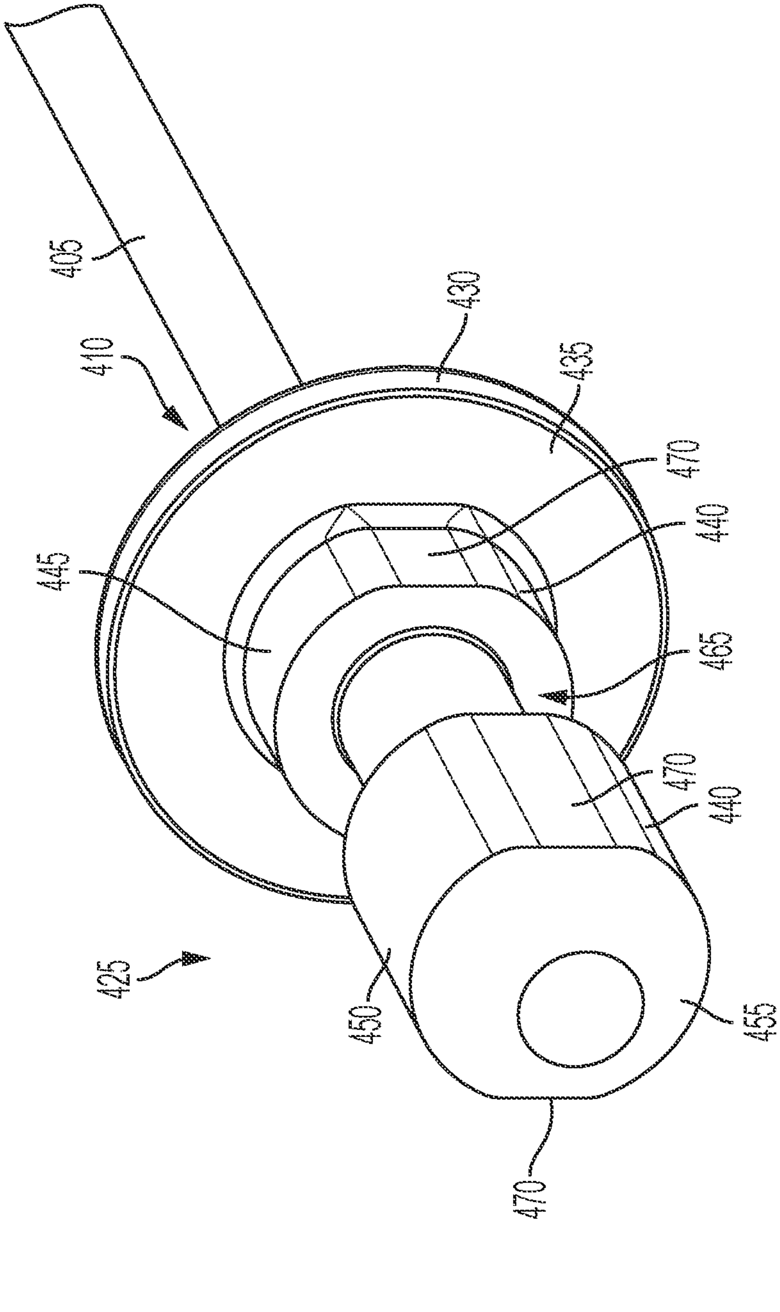
FIG. 4 is an enlarged perspective view of a connector of the bit of FIG. 3.
Figure 5:
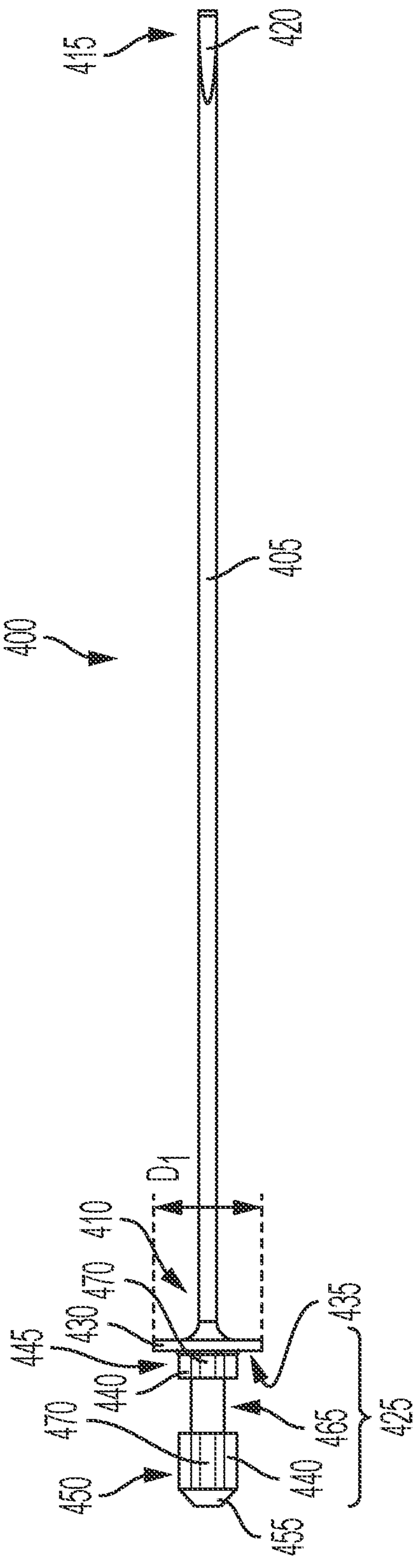
FIG. 5 is side view of the bit of FIG. 3.
Figure 6:
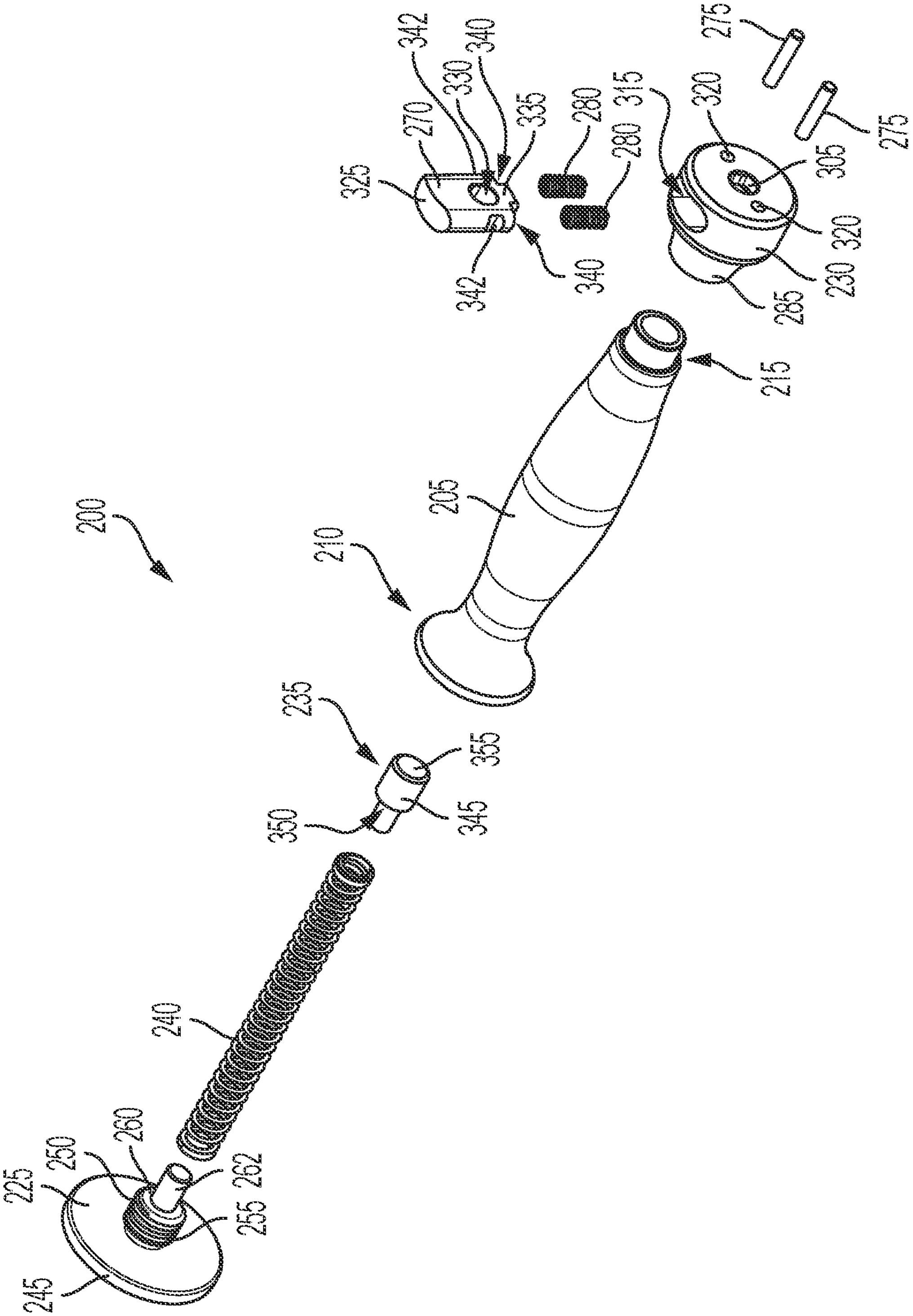
FIG. 6 is an exploded perspective view of a handle of the surgical tool of FIG. 1.
Figure 7:
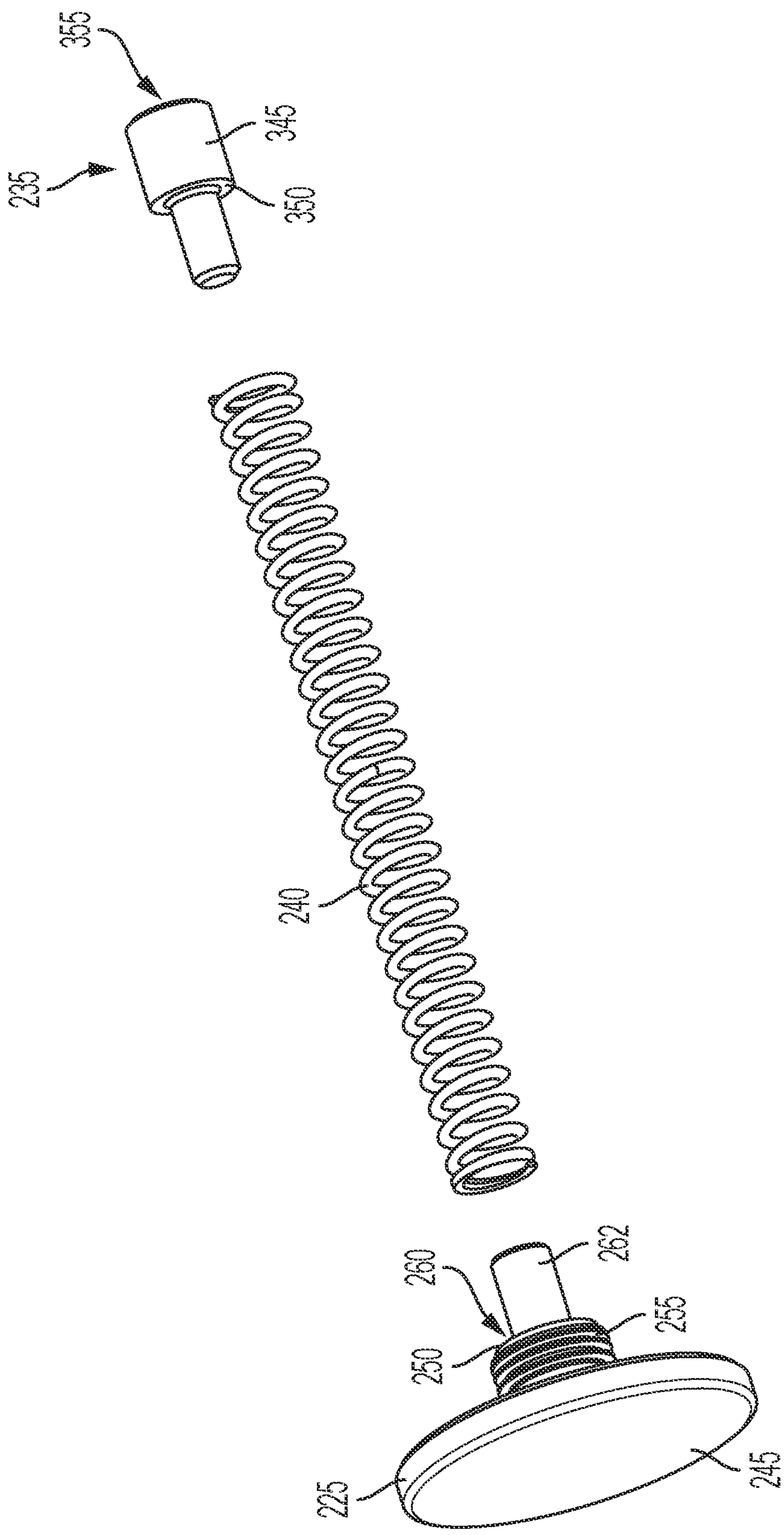
FIG. 7 is a perspective view of a cap, a biasing member and a plunger of the handle of FIG. 6.
Figure 8:
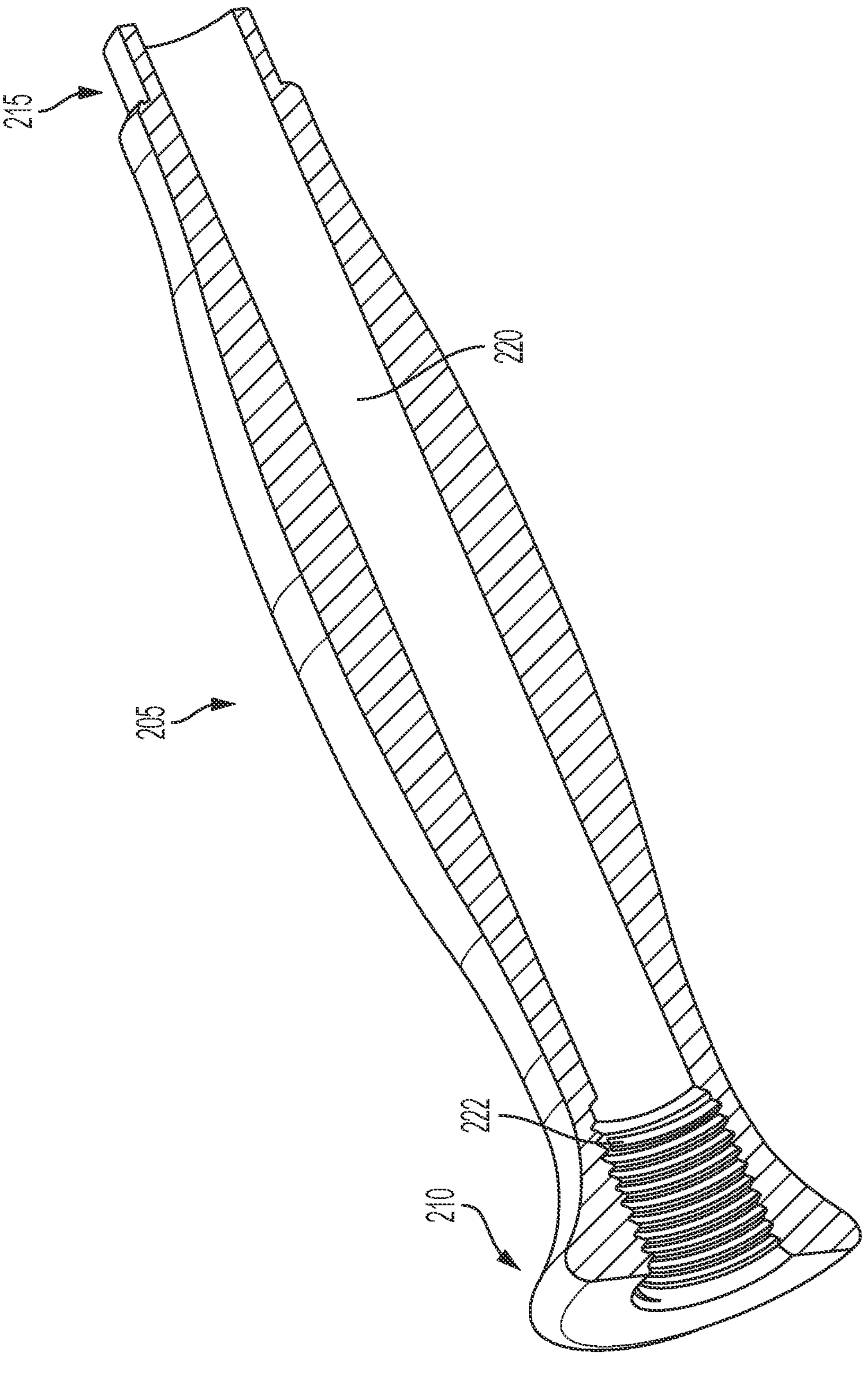
FIG. 8 is a sectional perspective view of a grip of the handle of FIG. 6.
Figure 9:
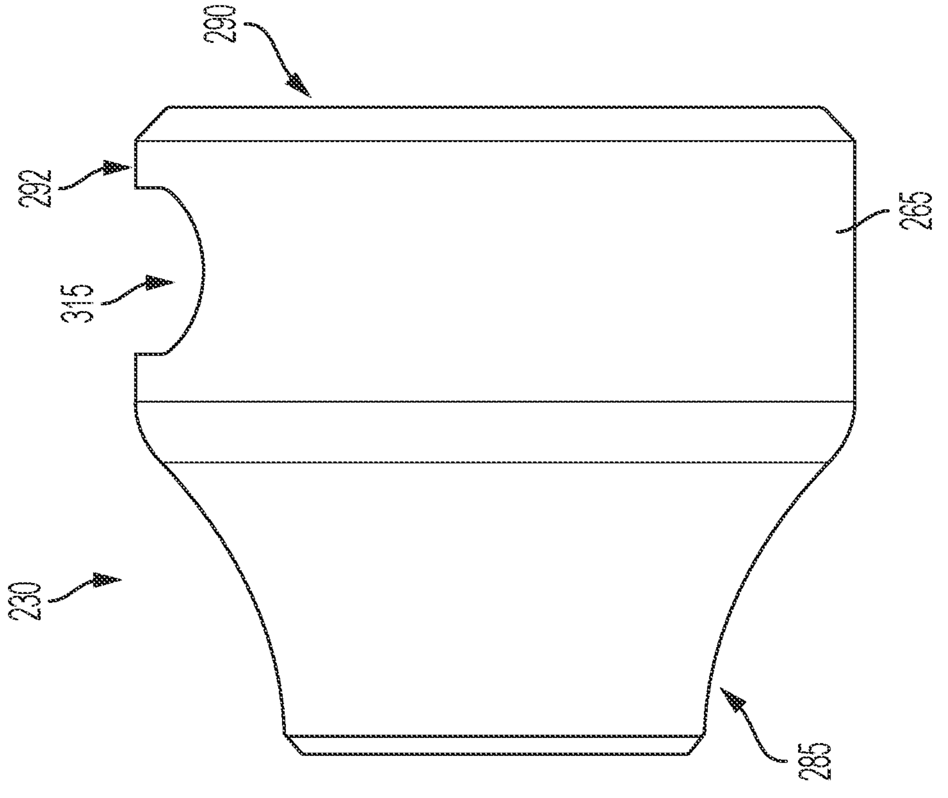
FIG. 9 is a side view of a coupler of the handle of FIG. 1.
Figure 10:
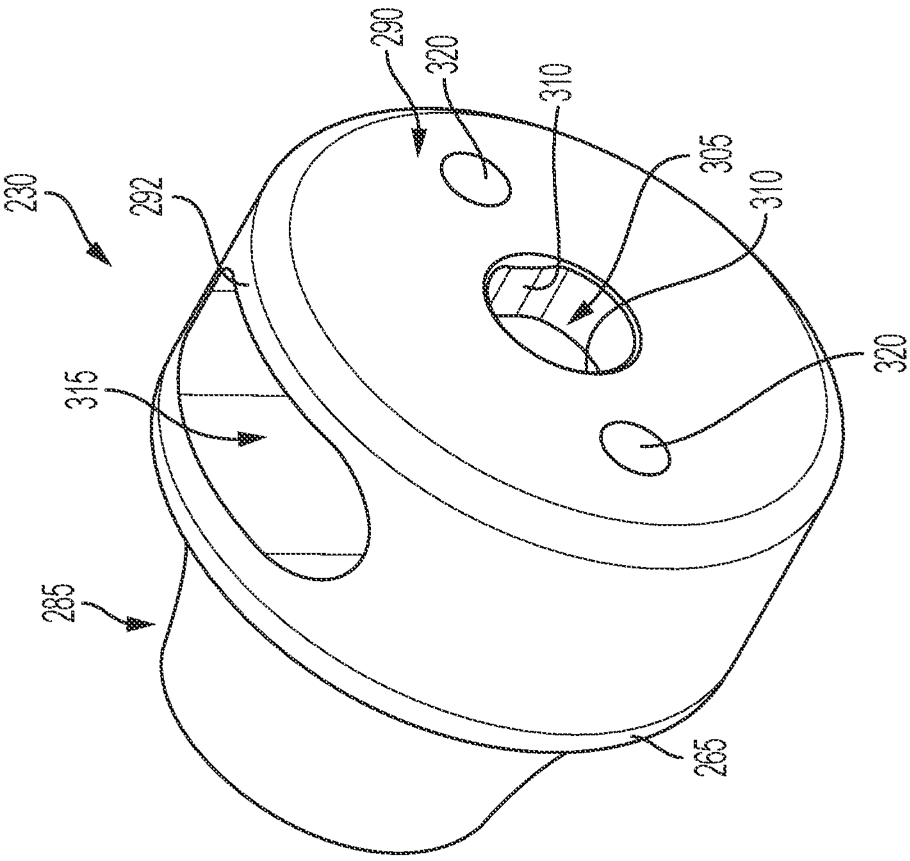
FIG. 10 is a perspective view of the coupler of FIG. 9.
Figure 11:
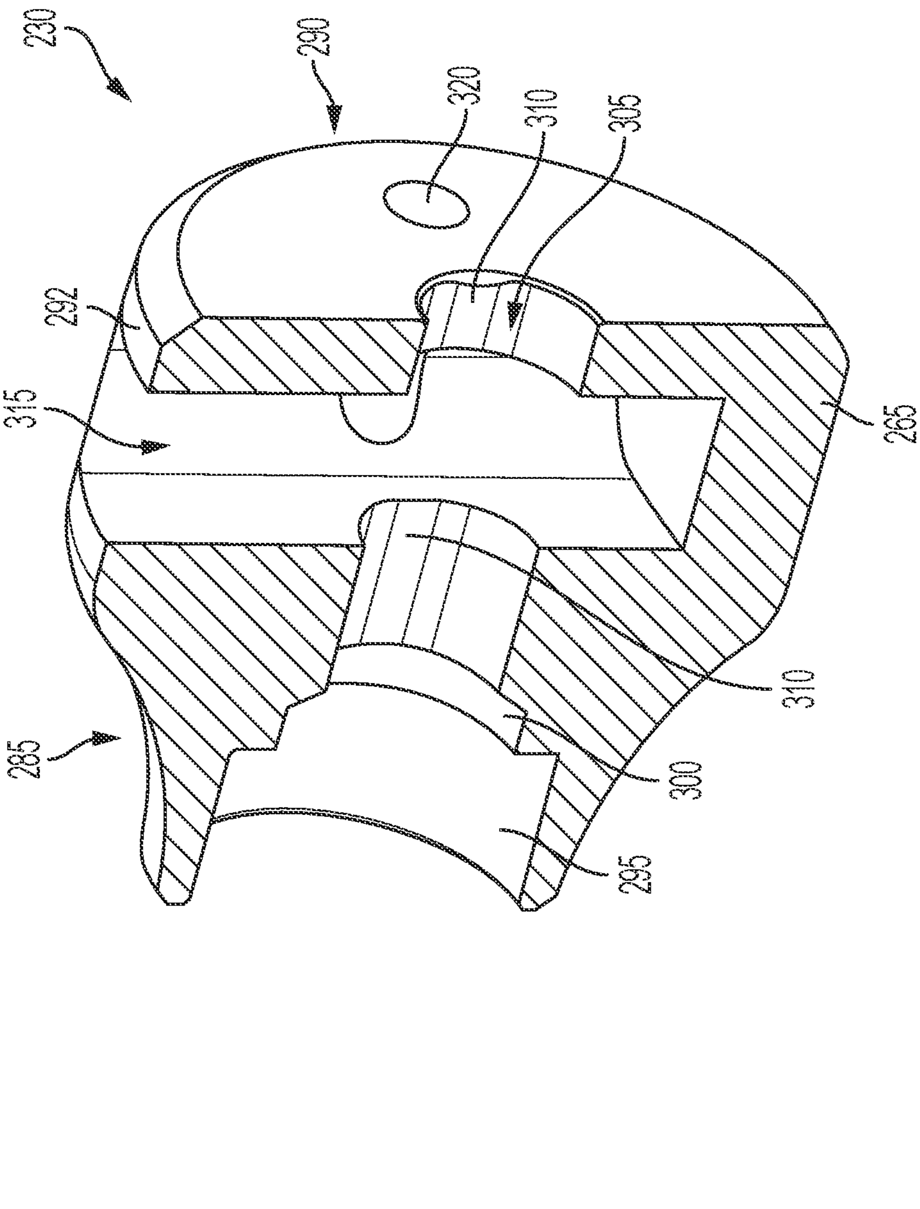
FIG. 11 is a sectional perspective view of the coupler of FIG. 9.
Figure 12:
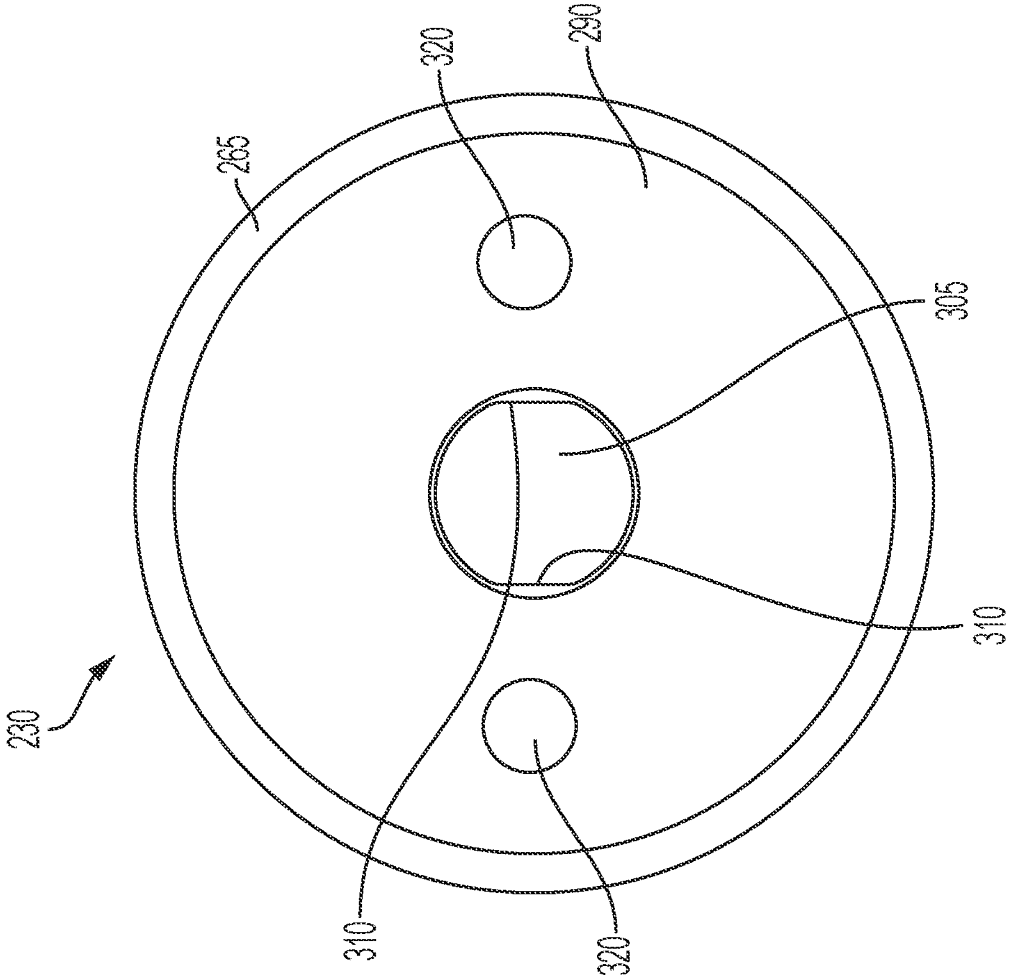
FIG. 12 is a front view of the coupler of FIG. 9.
Figure 13:
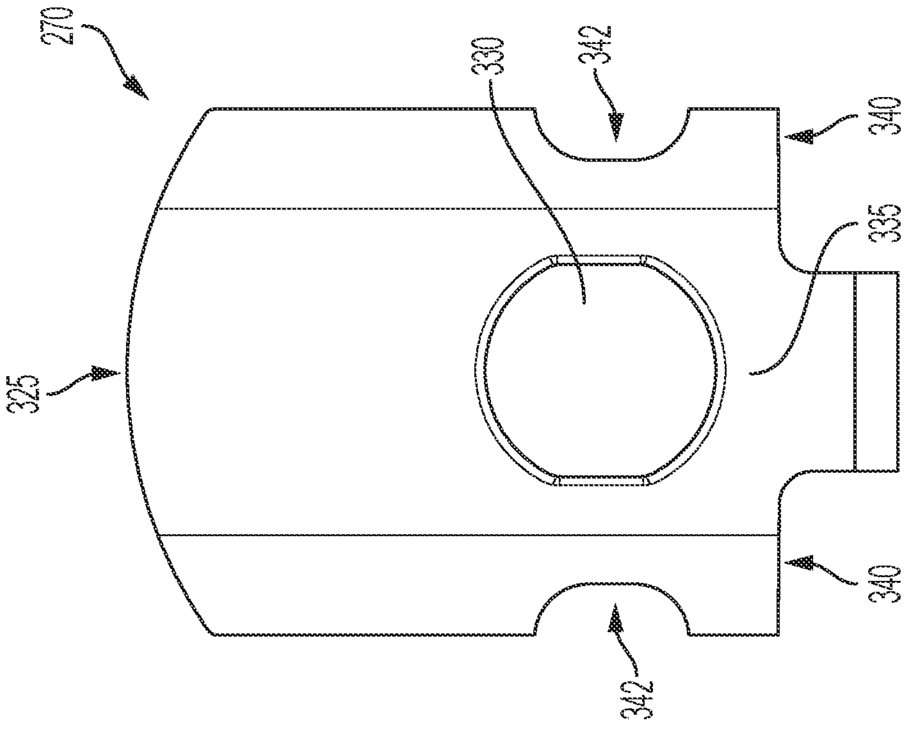
FIG. 13 is a front view of a button of the coupler of FIG. 9.
Figure 14:
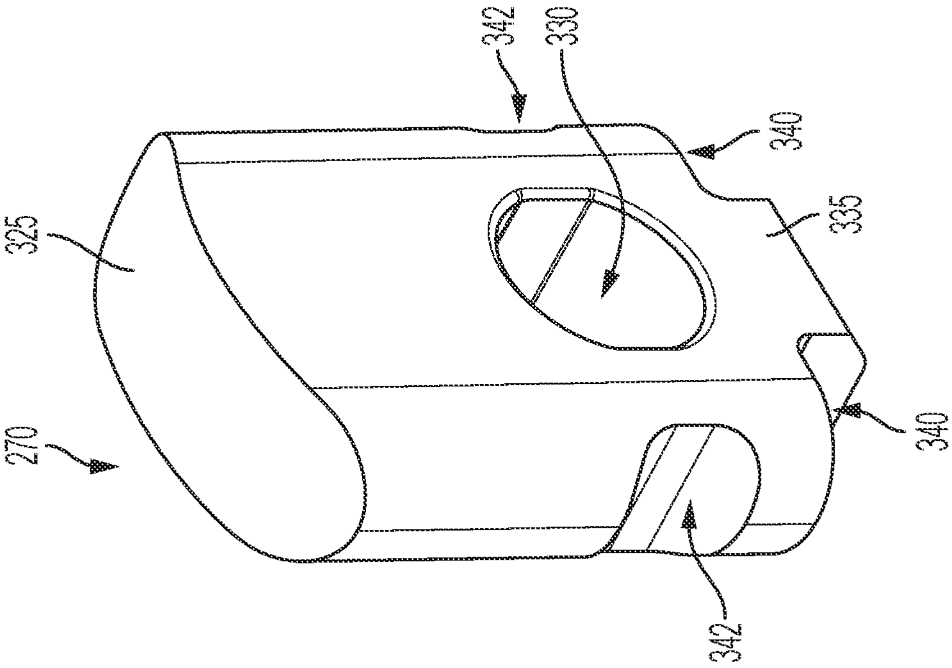
FIG. 14 is a perspective view of the button of FIG. 13.
Figure 15:
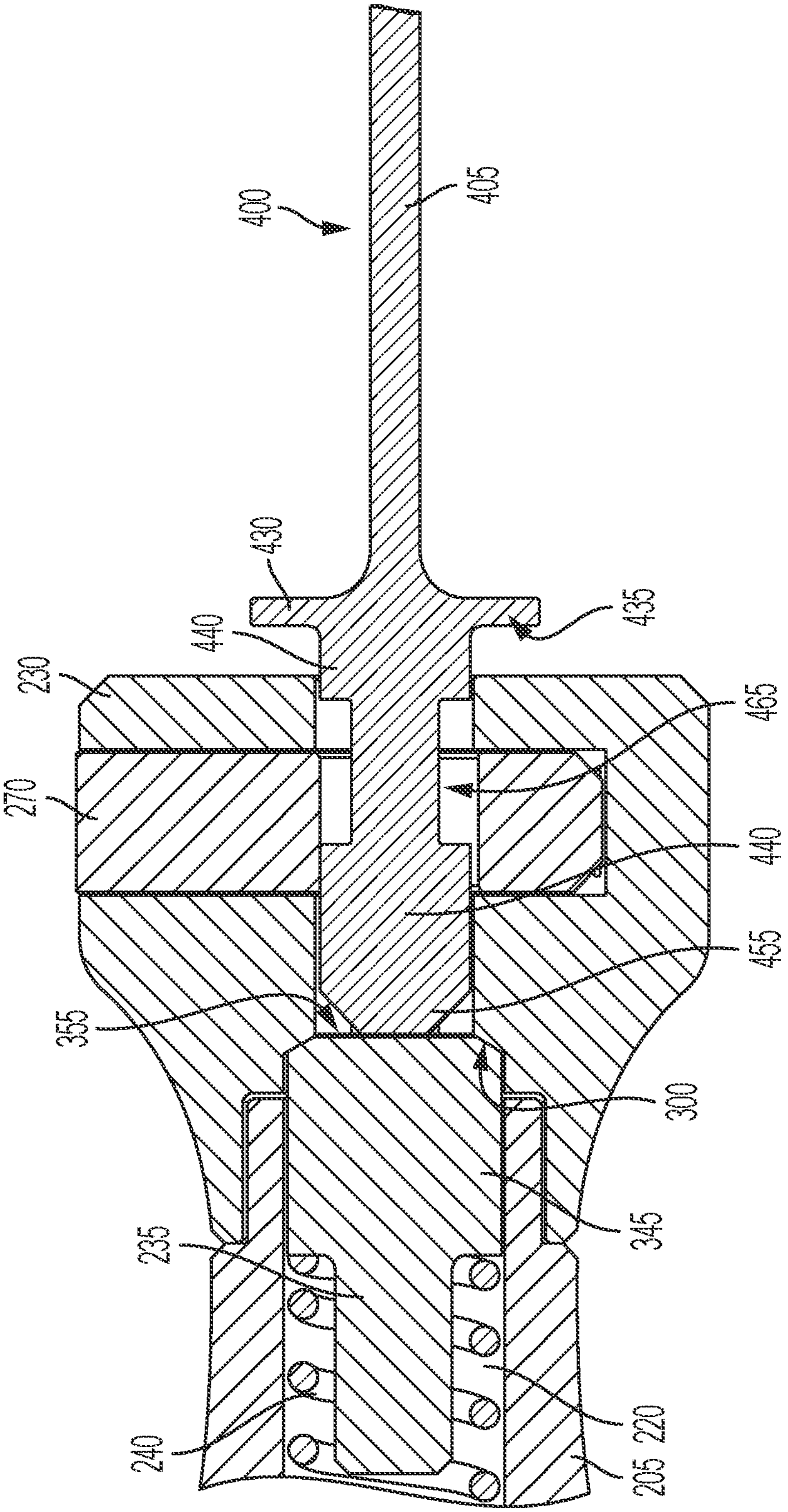
FIG. 15 is an enlarged partial side sectional view of the surgical tool of FIG. 1 with a partially inserted bit.
Figure 16:
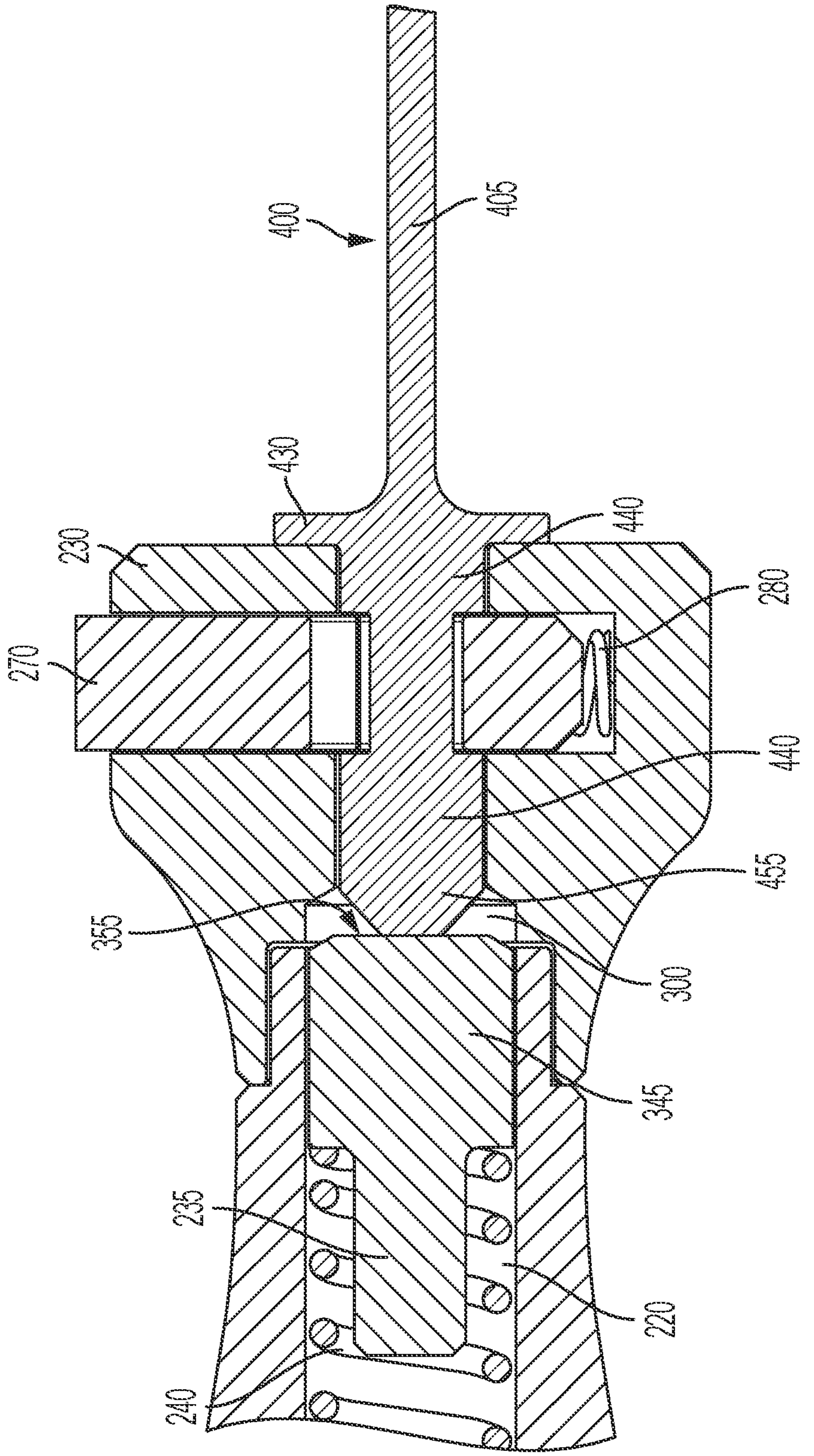
FIG. 16 is an enlarged partial side sectional view of the surgical tool of FIG. 1 with a fully inserted bit.

Referring to FIGS. 2 and 8, the plunger 235 is slidably positioned within through-bore 220 of grip 205. As shown in FIG. 7, the plunger 235 includes a main barrel 345 having a proximally facing annular face 350 and a distally facing engagement surface 355. First biasing member 240 is also positioned within through-bore 220 between stop 250 of cap 225 and annular face 350 of plunger 235. As shown in FIG. 15, when bit 400 is removed from or otherwise not locked to coupler 230, first biasing member 240 biases plunger 235 distally into plunger receptacle 300. As best shown in FIG. 16, when bit 400 is inserted and locked within coupler 230, tapered cone 455 of bit 400 contacts engagement surface 355 and urges plunger 235 proximally within through-bore 220 of grip 205 against the biasing force exerted by first biasing member 240. This, in turn, causes plunger 235 to exert an equal and opposite force distally against tapered cone 455 of bit 400, thereby urging a proximal side of locking channel 465 firmly against locking tab 335 of button 270. In this manner, bit 400 is stabilized firmly with respect to handle 200 to the extent any loose play in fit between coupler 230 and connector 425 of bit 400 would otherwise result in undesirable longitudinal and/or lateral movement of bit 400 relative to handle 200.

Figure 17:
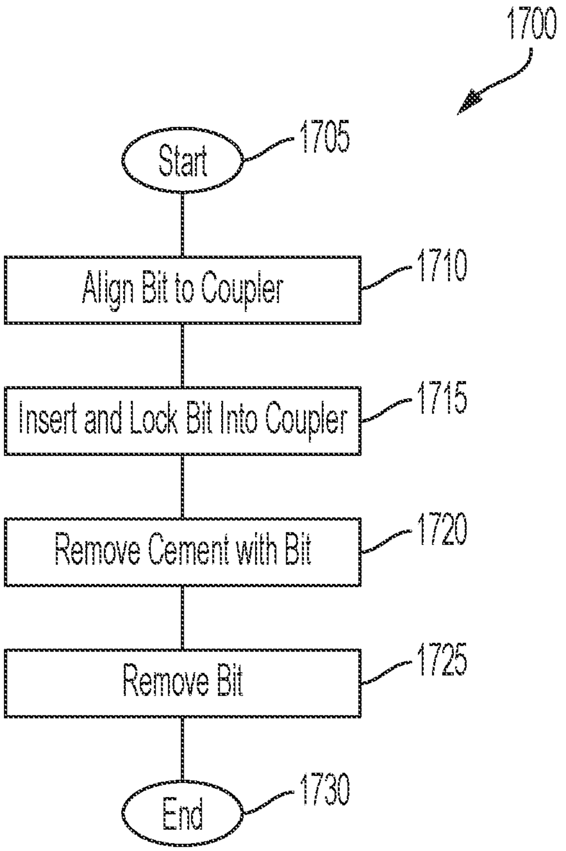
FIG. 17 is a flow diagram detailing a process of using the surgical tool of FIG. 1 to chip away cement of an implant to be removed.

Referring to FIG. 17, there is shown a flow diagram detailing a process 1700 for using surgical tool 100 in an orthopedic surgery to chip away bone cement of an implant to be removed. The process starts at step 1705 and proceeds to step 1710, at which a user rotationally aligns bit 400 relative to coupler 230 such that guide surfaces 470 of key 440 align with side surfaces 310 of longitudinal bore 305. Then, at step 1715, the user inserts key 440 of bit 400 proximally into longitudinal bore 305. As bit 400 is inserted, the surface of tapered cone 455 of key 440 engages locking tab 335 of button 270, causing button 270 to displace downwardly into the lower unlocked position against biasing forces exerted by second biasing members 280. Insertion of bit 400 continues until the proximal end of tapered cone 455 contacts engagement surface 355 of plunger 235. Further insertion of bit 400 proximally into longitudinal bore 305 causes plunger 235 to displace proximally within through-bore 220 of grip 205 against the biasing force of first biasing member 240 until locking channel 465 of bit 400 aligns with locking tab 335 of button 270, at which point second biasing members 280 bias button 270 upwardly into the upper locked position. This causes locking tab 335 to engage locking channel 465 of bit 400 to maintain bit 400 firmly within coupler 230. The process then proceeds to step 1720, at which the user employs surgical tool 100 to remove cement of the implant to be removed. For this purpose, the user positions tapered blade 420 against the cement and impacts strike plate 245 repeatedly with a mallet, surgical hammer or like device to chip away the cement. The impact forces applied to surgical toll 100 substantially bypass the internal mechanisms of handle 200, being transferred instead through grip 205 and coupler 230 and directly to face 435 of bit 400. After the cement is chipped away and the implant removed, the process proceeds to step 1725, at which the user removes bit 400 by first depressing and sliding button 270 into the lower unlocked position, at which point the user manually removes bit 400 from longitudinal bore 305 of coupler 230. Removal of bit 400 may be facilitated also by biasing forces exerted by first biasing member 240 and plunger 235 against tapered cone 455 of bit 400. The process then ends at step 1730.

It should also be appreciated by those skilled in the art that changes may be made to the exemplary embodiments described above without departing from the broad inventive concept thereof. It is to be understood, therefore, that this disclosure is not limited to the particular exemplary embodiments disclosed, but it is intended to cover modifications within the spirit and scope of the claims defined herein.

What is claimed is:

1. A handle for a surgical tool, comprising:

a grip having a proximal end, a distal end and a through-bore, a bit coupler positioned at the distal end of the grip, a plunger slidably positioned within the through-bore of the grip, and a first biasing member in the through-bore of the grip to bias the plunger distally into continuous contact with the bit coupler, wherein the bit coupler has a proximal facing annular surface longitudinally fixed adjacent the distal end of the grip.

2. The handle of claim 1, further comprising a quick connect about its distal end.

3. A surgical tool, comprising:

the handle of claim 1, including:

a bit releasably coupled to the bit coupler of the handle.

4. The surgical tool of claim 3, wherein the bit is a chisel bit.

5. The surgical tool of claim 3, wherein the bit coupler comprises a longitudinal bore and the bit includes a key releasably lockable in the longitudinal bore.

6. The surgical tool of claim 5, wherein the longitudinal bore has a cross-section sized to substantially match that of the key.

7. The surgical tool of claim 6, wherein the longitudinal bore and the key are substantially oval-shaped.

8. The surgical tool of claim 5, wherein the key includes a proximal end, a distal end, and a mid-portion circumscribed by a locking channel.

9. The surgical tool of claim 8, wherein the bit coupler further comprises a button slidably positioned in the bit coupler.

10. The surgical tool of claim 9, wherein the button includes a bore alignable with the longitudinal bore of the coupler and a locking tab releasably engageable with the locking channel.

11. The surgical tool of claim 10, further comprising a second biasing member for biasing the locking tab into engagement with the locking channel.

12. The surgical tool of claim 11, wherein, when the bit is inserted and locked within the bit coupler, the first biasing member biases the plunger to exert force against the bit.

13. The surgical tool of claim 3, further comprising a cap coupled to the proximal end of the grip.

14. The surgical tool of claim 13, wherein the cap includes a strike plate.

15. The surgical tool of claim 13, wherein the cap includes threads for threadedly engaging threads provided on the grip.

16. The handle of claim 1, wherein the first biasing member biases the plunger distally into continuous contact with the proximal facing annular surface of the bit coupler.

17. A handle for a surgical tool, comprising:

a grip having a proximal end, a distal end and a through-bore, a bit coupler positioned at the distal end of the grip, a plunger slidably positioned within the through-bore of the grip, and a first biasing member in the through-bore of the grip, wherein:

when a bit is non-existent, removed, or is not lockingly engaged to the bit coupler, the first biasing member biases the plunger distally into contact with the bit coupler; and when a bit is lockingly engaged to the bit coupler, the first biasing member biases the plunger distally into contact with a proximal end of the bit.

18. The handle of claim 17, wherein the contact when the bit is lockingly engaged to the bit coupler is a continuous abutting contact.

19. The handle of claim 17, wherein the contact when the bit is lockingly engaged to the bit coupler is a direct contact.

20. A surgical tool, comprising:

the handle of claim 17; and a bit configured to be releasably and lockingly engageable to the bit coupler.

21. The handle of claim 17, wherein, when a bit is inserted into, approaches and enters locking engagement with, the coupler, the proximal end of the bit contacts a distal end of the plunger and proximally urges the plunger within the through-bore against biasing force exerted by the first biasing member, causing the plunger to exert an opposite force distally against the proximal end of the bit, thereby urging a biased locking engagement between the coupler and the bit.

* * * * *